United States Patent [19]

Fipke

[11] 4,193,767

[45] Mar. 18, 1980

[54] PARTICULATE MINERAL SEPARATION PROCESS

[76] Inventor: Charles E. Fipke, 263 Lake Ave., Kelowna, British Columbia, Canada

[21] Appl. No.: 954,754

[22] Filed: Oct. 26, 1978

Related U.S. Application Data

[63] Continuation-in-part of Ser. No. 804,541, Jun. 8, 1977, abandoned.

[51] Int. Cl.² ............................................. G01N 33/24
[52] U.S. Cl. .................................. 23/230 EP; 209/12; 209/39; 209/40; 209/172
[58] Field of Search ..................... 209/3, 5, 9, 11, 237, 209/17, 12, 18, 10, 13, 8, 172, 39, 40; 23/432 PS, 230 EP

[56] References Cited

U.S. PATENT DOCUMENTS

| 956,381 | 4/1910 | Lockwood | 209/9 X |
|---|---|---|---|
| 1,999,825 | 4/1935 | Saklatwalla et al. | 209/12 X |
| 2,240,718 | 5/1941 | Schiffman et al. | 209/11 X |
| 2,514,958 | 7/1950 | Lee | 209/18 |
| 3,308,946 | 3/1967 | Mitzmager et al. | 209/172 X |
| 3,463,310 | 8/1969 | Ergun et al. | 209/11 X |
| 3,936,372 | 2/1976 | Frangiskos | 209/11 X |

FOREIGN PATENT DOCUMENTS 1157563  11/1963  Fed. Rep. of Germany .............. 209/9

Primary Examiner—Ralph J. Hill
Attorney, Agent, or Firm—Christensen, O'Connor, Johnson & Kindness

[57] ABSTRACT

A method used in conjunction with prospecting or mineral exploration of sedimentary deposits containing a minute amount of an economic mineral is described. The method is applied to a bulk sample of a deposit and generally involves the steps of washing and wet sieving the sample to produce two or more size fractions, drying the size fraction, separating at least one size fraction into at least two specific gravity fractions and, usually, magnetically separating at least one specific gravity fraction for the purpose of obtaining economic mineral concentration in at least one fraction of such sample. For specific environments where unstable sulphide conditions exist, an acid leach step may be included following specific gravity separation either to a specific gravity fraction or to a fraction resulting from magnetic separation after specific gravity separation.

40 Claims, 3 Drawing Figures

PARTICULATE MINERAL SEPARATION PROCESS

This application is a continuation-in-part of Application Ser. No. 804,541, filed June 8, 1977, now abandoned.

This invention relates to the field of mineral exploration. More particularly, this invention relates to methods of processing bulk samples of loosely consolidated or unconsolidated "sievable" sedimentary deposits to obtain fractions of such samples which fractions are suitable for analysis by means of a variety of conventional analytical techniques to detect anomalous economic mineral concentrations in the fractions. The samples normally contain only a minute amount of the economic mineral or mineral. Herein, the term "mineral" or "minerals" includes weathering products of the mineral or minerals.

A common method of processing a bulk sample of a sedimentary deposit is to simply screen the sample to produce a size fraction consisting of particles not greater than a predetermined size. Often, the size fraction selected will be of the order of −80 mesh. For the purpose of concentrating metallic or sulphide minerals which occur in bulk samples of stream sediments or sedimentary deposits derived from the erosion of geologic environments containing mineral deposits, somewhat more involved processes have been used. For example, it has been shown that hand panned, −80 mesh, bromiformed, non-magnetic heavy mineral concentrates of some stream sediments in the dispersion train of some mineral deposits will, upon analysis, produce an accentuated and longer geochemical dispersion compared with conventional −80 mesh concentration techniques. Such methods are thought to reduce occurences where dilution by waste or uneconomic particles (viz. gangue) results in economic mineral deposits not being detected by conventional geochemical techniques. However, despite the advantage of such methods, several geologic-climatic environments have been found where the methods were ineffective at concentrating ore minerals, and there was little or no advantage over conventional geochemical techniques.

The ineffectiveness of such heavy mineral concentration methods may be attributed to a number of different reasons. Firstly, sulphide minerals and some other metallic minerals are easily floated, and gossan particles are easily washed away during hand panning with water. Combining such problems with the inherent problems of human inconsistency can result in little or no effective concentration.

Another common problem occurs when the geologic environment being sampled contains paramagnetic minerals such as epidote or garnet. High proportions of such minerals can become concentrated with heavy particles thereby affecting background or only weakly anomalous geochemical responses in the sedimentary dispersion of mineral deposits.

An object of the present invention is to provide a method of processing a sample of a sedimentary deposit in conjunction with an exploration survey in a manner which, compared to conventional techniques, increases the likelihood that economic mineral particles will be effectively concentrated so as to better enable detection of such particles upon analysis.

It is a further object of the present invention that such method is uncomplicated and easy to implement using equipment and materials which are ordinarily readily available.

In the present invention, it has been found that the problems associated with hand panning can be overcome by instead using a combined washing and wet sieving process in water, preferably in a manner that reduces particle cohesion and metallic mineral loss through processes of flotation. Furthermore, the problem of dilution of metal bearing heavy particles by heavy gangue particles can be overcome by sizing combined with heavy liquid specific gravity separations and in most cases with magnetic separations.

In accordance with the present invention, a sievable sample of a sedimentary deposit is divided into a number of sample fractions, each of which fractions is characterized by size, by size and specific gravity, or by size, specific gravity and magnetic characteristics. For most applications, it is contemplated that the method of the present invention will preferably comprise a washing and wet sieving stage, a drying stage, a stage with two heavy liquid specific gravity separations, a further washing and drying stage, and a magnetic separation stage involving a hand magnetic separation stage and an electromagnetic-gravitational separation stage. However, as will become apparent, the method used in particular applications may vary somewhat. For example, in some applications there may be only one heavy liquid specific gravity separation. Likewise, in some specific applications there may be no magnetic separation stage. In some applications it has been found particularly advantageous to include an acid leach step which, depending upon the climatic-geological environment of the sedimentary deposit (discussed in more detail hereinafter), can substantially increase geochemical contrasts thereby enhancing probability of detection.

Herein, it is to be understood that the word "sievable" in reference to a sample indicates that the sample comprises particles of size generally less than 6 mesh. In most cases, it is contemplated that the sample will comprise particles of a size generally less than 10 mesh. However, some minerals, such as diamond indicators may fall within the 6 to 10 mesh range. It is also to be understood that the present invention contemplates, in some cases, that a sample in the form originally retrieved may in fact be in a semi-consolidated state. For example, sediments collected from a dry creek bed may have been in semi-consolidated state while in situ. In such cases, it is to be understood as implicit that, prior to the application of the present invention, the semi-consolidated particles are loosened (viz. as by agitation or light crushing) to separate the particles to an unconsolidated state.

For a given application, the steps followed in the practise of the present invention, and the number and character of the resultant sample fractions produced for subsequent analysis, may depend on the nature of the exploration survey being conducted. If the geologic and weathering characteristics of a sedimentary area under consideration are unknown or complex, it will be usual to conduct one but preferably more orientation surveys. In such surveys bulk samples of sievable sediments are collected outward from and within a sedimentary dispersion of the type of mineral deposit or deposits which are sought to be discovered. Apart from the size of particles (i.e. less than six mesh), no assumptions are made as to which fraction or fractions of the samples may yield the best geochemical contrast and dispersion. A relatively large number of sample fractions characterized differently by size, size and specific gravity, or size, specific gravity and magnetic characteristics, will desirably be produced. The fractions are then submitted to chemical and in some cases mineralogical analysis. There are a variety of well known techniques for analysis including, for example: chemical assaying, X-ray analysis, Geiger counter analysis, ultraviolet light analysis, microscope analysis, isotopic analysis and spectrometric analysis. Since such techniques are well known, they will not be discussed in detail herein. The results of an orientation survey, or the combined results of two or more orientation surveys, reveal which size, specific gravity, and magnetic fractions produce the strongest geochemical contrast from background or threshold levels and longest disperson in the environment sampled.

In some situations, it may be decided to conduct a reconnaissance survey rather than an orientation survey. A reconnaissance survey may be conducted in circumstances where the results are available from an orientation survey in a similar climatic and topographic, but not necessarily geologic, environment. Here, based upon the results of the orientation survey, the method of the present invention may be limited to producing only the sample fraction or fractions which produced the best geochemical contrast and dispersion in the orientation work. Depending upon the results of the orientation work, fewer specific gravity separations may be made. Similarly, again depending upon the results of the orientation work, it may be decided that no significant improvement in the results of the reconnaissance survey are to be expected by producing magnetic fractions—in which case the step of magnetic separation would of course not be applied to samples taken during the reconnaissance survey.

As is true of known techniques for exploration sampling, it cannot be said that the production of sample fractions in accordance with the present invention, and subsequent analysis of such fractions, will invariably result in the detection of economic minerals which are sought to be detected. However, it is considered that the present invention as a method used in conjunction with exploration sampling represents a significant improvement over conventional techniques because the sample fractions produced in the practise of the invention, when analyzed, are more likely to produce an accentuated and longer geochemical dispersion than is apt to be produced using conventional techniques. Thus, it is more likely that economic mineral deposits will be detected. Further, it is considered that the method of the present invention is uncomplicated and easy to employ—considerations which are significant in exploration sampling where cost and often time are important.

The invention will now be described in more detail with reference to the drawings in which.

Figure 1:
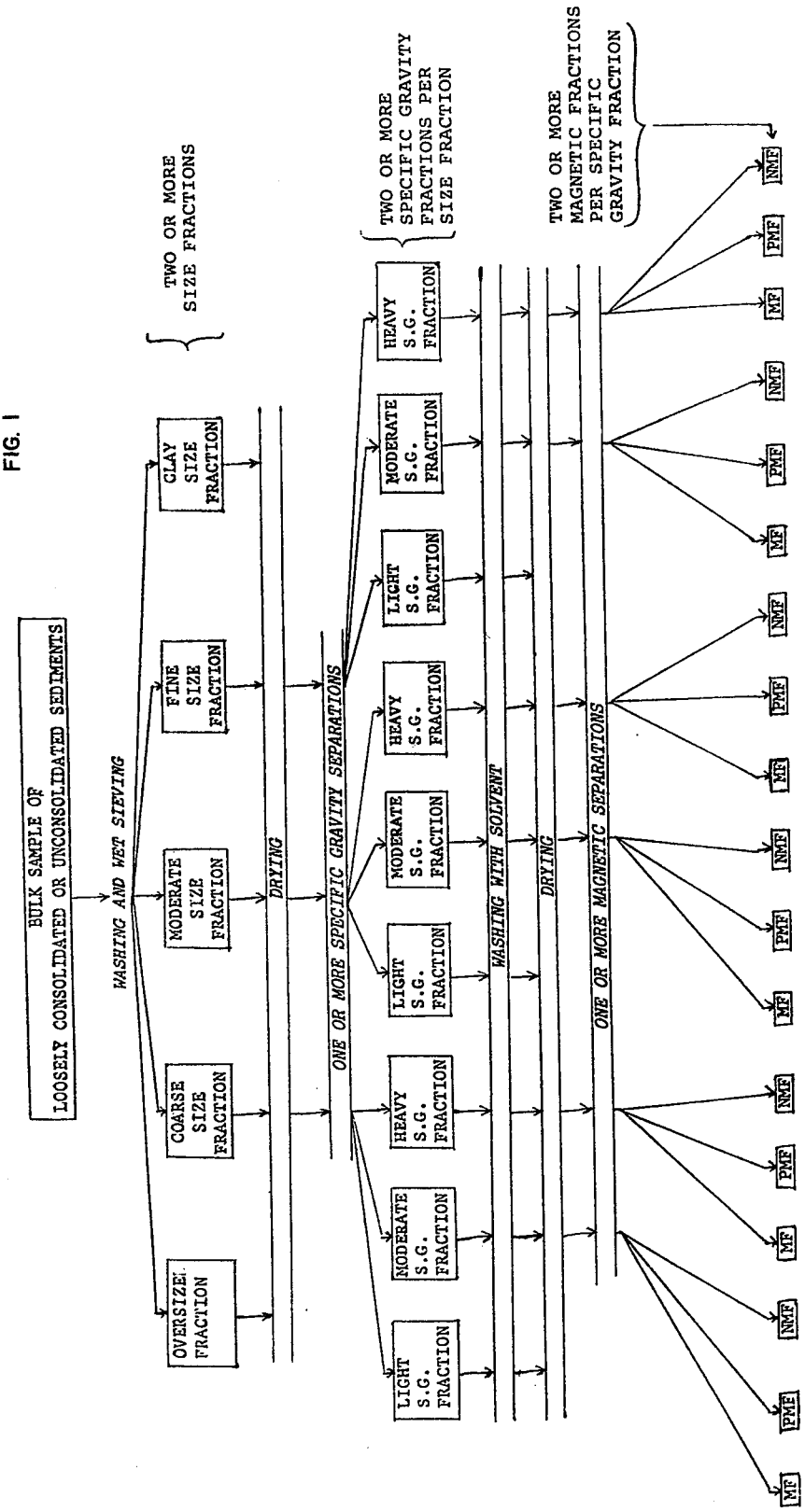
FIG. 1 is a generalized flow chart showing an example of typical steps involved and sample fractions isolated during the practise of the present invention in conjunction with an orientation survey.

Referring now to the drawings, FIG. 1 shows the processing which a sample of loosely consolidated or unconsolidated sediments containing a minute amount of economic minerals may typically undergo in conjunction with an orientation survey. The sample may be, for example: a sample of stream sediments, a sample of a sand dune deposit, a sample of a glacial drift deposit, or a sample of soil sediments.

The sample is first submitted to a washing and wet sieving stage using water. Preferably, the water includes a chemical additive which acts to reduce any particle cohesion and to reduce the surface tension of the water. It has been found that liquid detergent soap or an alkaline emulsifying agent can be a suitable additive. When water is available for use, the sieving can be implemented entirely in the field, or entirely in the laboratory, or in part in the field and in part in the laboratory. Under field conditions, portable sieves or sieve sets are normally used, while under laboratory conditions mechanical sieve shakers are normally used.

The washing and wet sieving of the sample separates two or more size fractions of predetermined size. In general, for orientation surveys it will usually be desirable to separate more than two size fractions—FIG. 1 specifically depicts the separation of five fractions, namely, a clay size fraction, a fine size fraction, a moderate size fraction, a coarse size fraction, and an oversize fraction. The sieve sizes are somewhat arbitrarily predetermined in orientation surveys, but can be adjusted after mineralogic size studies to best suit the sampling conditions. For example, sieve sizes of 10, 20, 40, 60 and 80 mesh might be used initially, but subsequent analysis may reveal that the 40 to 60 and 60 to 80 mesh fractions contain the final size fraction yielding the highest geochemical contrasts. Microscopic size analysis of these two size fractions may indicate that most of the metal bearing material ranges between 45 and 75 mesh. Thus, in exploration sampling for new deposits under similar conditions, only the 45 to 75 mesh fraction need be isolated and processed further. Fractions which were undersize in relation to the 45 to 75 mesh fraction would be discarded or stored for possible future use.

Under all conditions, an object of the washing and wet sieving stage is to classify the sedimentary sample in a manner which minimizes particle cohesion and which minimizes metal particle loss through processes of flotation. It is preferable to wash and scrub the finest fraction in a manner which reduces particle cohesion and substantially removes relatively light, generally clay-sized particles. This may be accomplished in the following manner: by rubbing a fine fraction in water containing the chemical additive (e.g. detergent soap or alkaline emulsifying agent) by hand against the bottom pan or collective container of the sieve set used; by stirring the sample in the underwater state; by patting by hand any floating particles beneath the surface of water for a period of about 30 seconds which gives sufficient time to allow most clay sized limonites and sulphides to sink to the level of the sample overlying the pan; and by slowly pouring from the sample all but the last small remaining portion of water containing relatively light clay and organic particles. This process may be repeated using additional clean water until most of the clay and organic suspension are removed. Although much the same results can be accomplished by conventional desliming techniques, this is generally not preferred because very fine metal particles may be lost in the slimes.

The amount of sediment collected in orientation sampling is initially arbitrary, but generally sediments which contain 2 or more litres of −20 mesh sediments contain more than sufficient material. The amount of a particular size fraction used for processing is normally a function of the maximum amount that can be effectively separated during the first stage of heavy liquid separation. For example, if a conventional heavy liquid separation tube is to be used and its capacity is 500 ml of 45 to 75 mesh sediments, then only 500 ml of heavy sediments directly overlying the 75 mesh sieve would be retained for drying. The remaining mostly lighter upper excess layer would be either discarded or stored.

It is possible to remove these light excess particles by hand, by using a scooping tool such as a spoon, or by hand or mechanical panning. Panning of sized sediments, ideally with a mechanical panner to eliminate humanistic variance and with a chemical additive (e.g. detergent soap) to minimize sulphide flotation, while possible, is not preferred. This is because during sufficient sieve shaking with up-down and rotational actions, the desired heaviest portion of each size fraction will be already gravity concentrated near the surface of each restrictive sieve or near the surface of the basal container of the sieve set used. Thus each panning should be unnecessary. Of course hand panning would be even less desirable than mechanical panning. It might also be noted that panning of the fine size fraction produced on sieving is likely to effect losses of metal bearing clay sized limonite particles along with the light particles which overflow with panning.

Following the washing and wet sieving stage, the size fractions which have been produced and retained are submitted to an important drying stage. Drying is normally completed rapidly, either naturally utilizing the sun or in an oven at a low temperature, preferably less than 45° C. Slow drying over extended periods can cause the alteration of sulphide particles to limonites. Heating the sediments at elevated temperatures may cause the magnetic susceptability of metal limonite or gossan minerals to be increased. In general, such changes are undesirable, but one or both such changes can be deliberately caused in circumstances where it is considered desirable to do so. For example, in a highly specific geologic environment where there is a voluminous concentration of weakly paramagnetic gangue particles compared to a group of base metal bearing particles, principally in the limonite form, it may be desirable to magnetize the limonites in order to magnetically separate the metal and gangue particles. Similarly, pyrite and some other gangue minerals may be magnetized on sufficient heating. In environments where such gangue minerals are abundant, it may be desirable to remove them and thereby accentuate any geochemical response attributed to ore minerals in fractions of weak magnetic susceptibility.

If the dried samples are unconsolidated, they are then in condition for the stage of specific gravity separation. However, it may occur that light clays will not have been separated to the extent desired from the fine size fraction and, upon drying, will adhere in semi-consolidated state to particles of the fine size fraction. In such cases, it is advantageous to first reduce clay particle cohesion, preferably by resieving the semi-consolidated clay and fine size particles in a dry state through the fine size fraction sieve. This procedure will tend to strip the adhering clay particles from the fine size particles, and consequently permit the light clay particles to float during heavy liquid specific gravity separation.

As is illustrated in FIG. 1, a specific gravity separation stage follows the drying stage. Here, each size fraction which is submitted to specific gravity separation, is separated into two or more specific gravity fractions. As depicted in FIG. 1, the coarse size fraction, the moderate size fraction, and the fine size fraction, each undergo a two stage specific gravity separation. For each such fraction, a light specific gravity fraction (viz. light S.G. fraction), a moderate S.G. fraction, and a heavy S.G. fraction are produced. Typically, for example, a light S.G. fraction may consist of particles having a specific gravity less than 2.8 to 3.0, a heavy S.G. fraction may consist of particles having a specific gravity greater than 3.2, and a moderate S.G. fraction would consist of particles having a specific gravity intermediate the light S.G. fraction and the heavy S.G. fraction. The precise specfic gravity at which a separation is made can be varied somewhat and will be selected having regard to the specific gravity of the minerals of economic importance which are sought to be detected. The number of specific gravity separations made may be subject to time and cost considerations.

In many cases it is sufficient to complete a one state specific gravity separation through agitation and settling in a heavy liquid having a specific gravity of 3.2 to 3.3 Here, the light S.G. fraction would consist of particles having a specific gravity less than 3.2 to 3.3 and the heavy S.G. fraction would consist of particles having a specific gravity greater than 3.2 to 3.3. There would be no moderate S.G. fraction, intermediate the light and heavy S.G. fraction. The separation can be attained, for example, with pure methylene iodide or with methylene iodide diluted slightly with acetone. When all or nearly all the heavy sediments have settled out of the periodically agitated fluid, the sediments are drained unto filter paper utilizing a drain system device such as a clamped tube or a stop-cock. After the heavy particle sediments are thoroughly washed with solvent, they are dried, generally in a fume hood or in an oven according to the previously discussed condition of drying. The steps of washing with solvent and subsequent drying are depicted generally in FIG. 1. The light particles are then separated, preferably in the same manner as the heavy particles. Much of the methylene iodide is recoverable by filtration and/or by evaporation of any solvent present.

However, it is preferred to complete a two stage heavy liquid separation consisting firstly of a primary separation at a specific gravity of 2.8 to 3.0 with a liquid such as tetrabromethene or bromiform, or a solution of acetone and methylene iodide. This is implemented in a manner similar to the one stage approach, but using a liquid of lower specific gravity. This step is followed by a separation of the resultant heavy fraction according to the process described above utilizing a liquid having a specific gravity of 3.2 to 3.3.

Although the two stage approach can be a little more time consuming, less of the relatively expensive heavy liquid, methylene iodide, will ordinarily be lost when bromiform or the even more economical liquid, tetrabromethene, is used for the primary separation. In fact, the economics of using the less expensive liquids permits the use of more voluminous separation containers, thus enabling the treatment of increased amounts of sediments and thereby reducing the chances of failing to concentrate economic mineral particles from the sediments. When the heavy minerals undergo the second separation at a specific gravity greater than 3.2, the sample size is smaller and, probably attributable to decreased interference by light particles, the relative concentration of metal particles is, as a rule increased over that concentrated with the single stage approach. Furthermore, an additional fraction, intermediate in specific gravity to the light S.G. fraction and the heavy S.G. fraction, is collected.

In many environments, metal assays on such intermediate S.G. fractions are significantly lower in magnitude compared with assays on the heavy S.G. fractions. However, in a specific weathering environment where, for example, a relatively large amount of sulphuric acid resulting from the breakdown of sulphides is produced, there is a tendency for light limonites or gossan particles to be formed in the intermediate specific gravity range.

In a specific environment where most of the sulphides or metallic minerals present were altered to such limonite minerals, it may be imperative to recover the limonite minerals. Recovery of the intermediate S.G. fraction by a two stage separation tends to ensure that virtually all economic metal bearing minerals will be concentrated.

Provided that the specific gravity separations have been implemented with some care, the light S.G. fraction should not contain significant economic heavy minerals. Therefore, even in orientation sampling, the light fraction is usually not separated further. Instead, a portion thereof is submitted in the dry state for assay as a check on the quality of separations and the remainder is stored.

However, in the event that light economic minerals such as minerals of berylium, lithium and/or coal are sought, it is normally necessary to have additional specific gravity and/or electromagnetic separations (discussed below) on the commonly voluminous, light S.G. fraction. Such separations are completed using the same concentration principles as used for higher specific gravity fractions except that the specific gravity separation mediums and the electromagnetic field settings are changed in accordance with the specific gravity and magnetic properties of the light, economic minerals which are sought to be concentrated.

After the fractions produced by specific gravity separation have been washed with solvent and dried, it will be usual to submit the clean, dry, unconsolidated concentrates of both the moderate S.G. fraction and the heavy S.G. fraction from orientation testing to magnetic separations where the ultimate objective is to produce a magnetic fraction, a paramagnetic fraction, and a non-magnetic fraction. In FIG. 1, the abbreviations "MF", "PMF" and "NMF" mean magnetic fraction, paramagnetic fraction, and non-magnetic fraction, respectively.

The magnetic fraction is first removed with the use of a covered hand magnet, a conventional separator for separating hand magnetic minerals, and/or an electromagnet set at a weak electromagnetic field setting. The object is to remove magnetic particles such as magnetite, chromite and pyrrhotite from the remainder of the fraction, the reason being that the presence of significant quantities of magnetic minerals unrelated to ore mineralization decreases geochemical contrast and dispersion thereby reducing the probability of ore detection. In addition, the presence of significant quantities of magnetic minerals tends to later plug some separators which utilize electromagnetic field principles. This then reduces the efficiency of separation of paramagnetic minerals from non-magnetic minerals.

The non-magnetic particles are separated from the paramagnetic particles by submitting the sample in a known gravitational field to an electromagnetic field. This can be accomplished with a number of known types of separators at optimum settings resulting in a removal of heavy particles of low magnetic susceptibility such as most native minerals, sulphides, base metal carbonates, and accessory minerals from particles of moderate magnetic susceptibility such as garnet, epidote, wolframite, monazite, limonite and ferromagnesium minerals. Different makes of separators, and even individual separators of the same make, may require different settings to accomplish the same job.

In orientation programs, all of the resultant magnetic, paramagnetic, and non-magnetic, sized, heavy mineral fractions are weighed, so that after geochemical assaying the combined assay of any two or more fractions can be computed. Typically, there may be 21 fractions per orientation sample, but this number may vary in accordance with the number of size, specific gravity and magnetic separations which are employed.

Depending on the types of mineral deposits which are sought, the fractions may be submitted to a variety of analytical techniques such as X-ray, Geiger counter, and/or ultraviolet light treatment. Later these fractions, the light S.G. fractions, the light clay size fractions and the oversize particles may be hand or mechanically split and 0.2 to 0.5 gram portions of fractions that are 80 mesh or finer are conventionally analyzed for the metal types being sought. Portions of fractions that are 80 mesh or greater are normally crushed to at least −80 mesh before assay.

The assay results of a complete orientation program are conventionally statistically analyzed to determine the fraction or combination of fractions which produce the highest geochemical contrast and longest geochemical dispersion to background or threshold. The unassayed portions of the high contrast fraction or fractions, as well as the unassayed portions of immediately undersize and immediately oversize fractions of the same magnetic-specific gravity type, can be sieved and/or microscopially studied to determine the upper and lower size limits of the contained metal bearing particles. This type of study is optional for the method is known to be successful without such refinements.

The foregoing procedure is applicable to most climatic-geological environments. However, in unstable sulphide conditions where mineral deposits develop thick leached cappings, or when utilizing oxidized glacial sediments, sulphide minerals may be entirely altered to limonite minerals that separate in paramagnetic fractions. If the geologic conditions are such that voluminous amounts of epidote, garnet, ferromagnesium minerals and/or other paramagnetic gangue minerals are concentrated in the paramagnetic fraction, geochemical metal contrasts can be weak or diluted below threshold. In such conditions, it has been found that a strong acid leach step applied either to paramagnetic concentrates or to size, specific gravity concentrated sediments that have undergone no or one magnetic separation, can be utilized to substantially increase geochemical contrasts—and thereby increase the probability of detection. In rare instances, it is contemplated that limonite coatings on magnetite will occur, in which case the acid leach step may be applied to a combined magnetic and paramagnetic fraction.

In the past, dry sieved sediments have been treated with oxidizing acids such as 1.5 N oxalic acid to produce leachates. Such treatments have not achieved widespread popularity as an exploration or reconnaissance tool because, if there are carbonates in the sediments sampled, the acids are neutralized and fail to liberate base metal values. In addition, the acids tend to consume clay minerals, particularly of the amorphous groups. As the clay content of sediments on a regional exploration program is variable, the gangue consumed by the acids is variable, and therefore, the analytical results are variable.

In applying a strong acid leach step to sink concentrates subsequent to the specific gravity concentration, any limestone or dolomite-carbonate type particles will have been removed from the concentrates. In addition, all or nearly all of the clay minerals will have been separated from the concentrates by the washing and wet sieving and specific gravity separation steps. As the concentrates consist mostly of resistant silicate or accessory minerals, strong acids can be applied without overwhelming proportions of gangue being consumed by the acids. This increases the chance of digesting goethitic limonites and other secondary minerals which are found to be resistant to weak acid attacks.

It has been found that resistant secondary minerals are substantially digested when the concentrates are submitted to a cold aqua regia digestion for a period of about two minutes, adding 2 N oxalic acid and boiling the acid mixture for about five minutes. About 3 ml of aqua regia and 10 ml of 2 N oxalic acid were used per gram of concentrate tested. The resultant acid solution was then filtered hot through a filter paper and evaporated to dryness in a crucible. Heating was continued in a muffle furnace of about 500° C. until the free oxalic acid was decomposed and the water of hydration driven off. After the leachate was cooled, it could then be ground and geochemically analyzed. As the proportion of any metals digested to gangue digested was greatly increased, geochemical contrast and therefore probability of detection was correspondingly increased.

If the acid leach step is utilized, it should only be applied to a portion of any sample being tested. As a result of the application of the step, chemical reactions can take place which will destroy or mask valuable background mineralogical information. It is therefore important to preserve a portion of any sample so that the background information will not be lost.

Reconnaissance sampling to discover deposits of similar mineralogy to that of the orientation survey or surveys is normally implemented in similar climatic and topographic but not necessarily geologic environments to those of the orientation work. In reconnaissance work, it is generally only necessary to isolate the size fraction containing sediments which produce the optimum geochemical contrasts and dispersion in the orientation work. This size fraction, or a portion of it, is then submitted to the previously described specific gravity separation or separations and drying procedures. Similarly, only those specific gravity separates which might contain meaningful results and/or contain a fraction or fractions known to give optimum geochemical parameters are submitted to the previous described magnetic fractionation or fractionations. The remaining specific gravity fractions are either stored or discarded.

Figure 2:
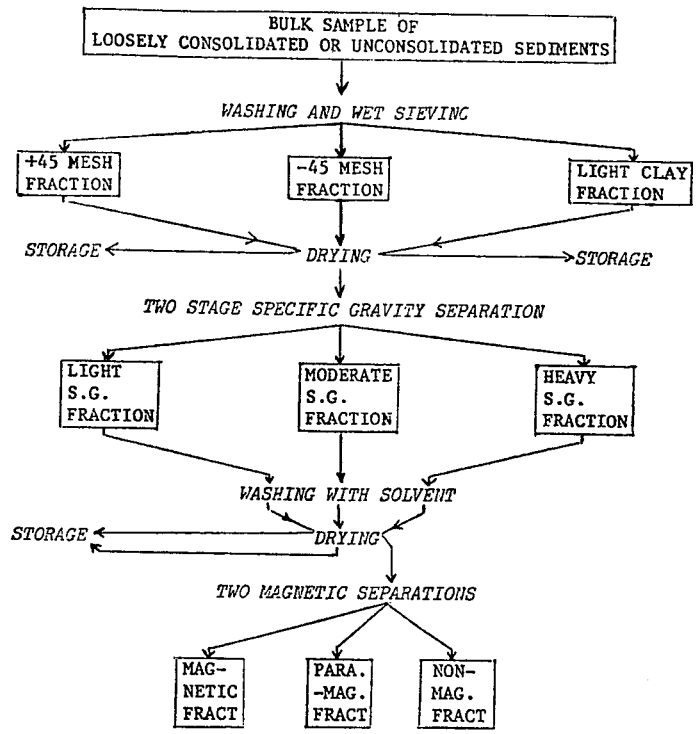
FIG. 2 is a flow chart showing an example of typical steps involved and sample fractions isolated during the practise of the present invention in conjunction with a survey where it has been predetermined that a −45 mesh, non-magnetic, heaviest specific gravity fraction produces the strongest geochemical contrast and dispersion.

FIG. 2 illustrates a case where it has been predetermined that a −45 mesh, non-magnetic, heaviest S.G. fraction produces the strongest geochemical contrast and dispersion. Therefore, as is shown in FIG. 2, only the −45 mesh size fraction without light clay separates, is submitted to further processing following washing and wet sieving and drying. As is also shown in FIG. 2, a +45 mesh fraction and a light clay fraction are also produced during the washing and wet sieving stage. These fractions are dried and stored for possible future use. Similarly, only the heavy S.G. fraction is submitted (following washing of the fraction with solvent and drying) to a two stage magnetic separation which produces the desired non-magnetic fraction. The light S.G. fraction and the moderate S.G. fraction are not magnetically separated, but are washed with solvent, dried and stored, again for possible future use. The case depicted in FIG. 2 is typical of a method engineered to overcome geological complexity under relatively uniform high energy climatic-hydrostatic conditions. In this method, final magnetic and/or paramagnetic particles are normally analyzed routinely with the non-magnetic fraction. This is a precaution which will increase the chances for detection when the mineralogic characteristics of the deposit to be detected differ from those of the orientation deposits.

Figure 3:
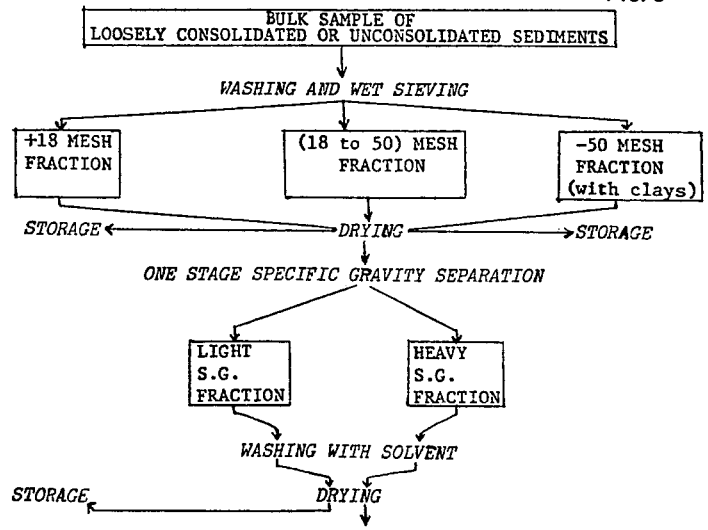
FIG. 3 is a flow chart showing an example of typical steps involved and sample fractions isolated during the practise of the present invention in conjunction with a survey where it has been predetermined that geochemical contrast and dispersion is not significantly increased by magnetic separation.

Only under the special conditions where it is known that the environment to be sampled is one of geologic and mineralogic simplicity, and where it is known that the inclusion of one or more magnetic fractionation products will not critically decrease the geochemical response of the remaining fractionation product or products, is it practical to eliminate one or more magnetic separations. An example of such a special case is illustrated in FIG. 3. In FIG. 3 it has been predetermined that a −18 to +50 mesh, heavy S.G. fraction is likely to produce the strongest geochemical contrast and dispersion, and that magnetic separation is not likely to significantly improve the results. It has also been predetermined that a one stage specific gravity separation to produce the desired heavy S.G. fraction is sufficient and that further specific gravity separations are not necessary. The heavy S.G. fraction as well as the light S.G. fraction is usually washed with solvent and dried; the light S.G. fraction is stored for possible future use. Similarly +18 mesh and −50 mesh fractions produced during the production of the −18 to +50 mesh fraction are stored for possible use following drying.

Normally after routine but optional Geiger counter and ultraviolet light treatment, a (0.2 to 0.5) gm portion of each resultant magnetic, paramagnetic and non-magnetic or specific gravity fraction is hand or mechanically split from the sample for chemical analysis. If the mesh size of the split sample is coarser than 80 mesh it is more practical to grind to 80 mesh or less. This permits increased chemical digestion. If the sample size is less than 80 mesh, it is more practical not to grind the sample because grinding small samples can give rise to significant perfential sample losses.

Anomalous metal responses above background or threshold levels are known to be attributable in magnetic fractions to the presence of mineral deposits with a mineralogic or a geochemical association to magnetite or magnetic minerals. An anomalous response in the paramagentic fraction of the intermediate specific gravity range may be attributable to a highly weathered deposite where the volume percent of sulphides is high and sulphuric acid is consequently liberated. An anomalous response in the paramagnetic fraction of the heaviest specific gravity range can be attributable to a highly weathered deposite undergoing weathering conditions of high pH or reflect paramagnetic mineralization such as wolframite, monazite, or pyrrhotite with pentlandite intergrowths. An anomalous response in the non-magnetic fraction generally results when pure and/or partially altered native metals, sulphides, or metal carbonates are present in the sedimentary dispersion sampled.

X-ray analysis can optionally proceed chemical analysis or be used as an alternative to chemical analysis. In this technique, the sample fractions are analyzed for crystalographic information which detects the presence and in some techniques, the quantities, of the economic minerals desired.

Binocular microscope studies can optionally be implemented on fractions giving rise to weak to strong X-ray and/or geochemical anomalies. Such studies as well as field float rock identifications help define priority rating for follow up work.

Isotopic studies can be optionally implemented on fractions giving rise to anomalous Pb values or Pb minerals. Such studies can serve to catagorize the type of Pb deposit detected and minimize unnecessary follow up work.

Modifications and variants of the foregoing will readily occur to those skilled in the art. The invention is not to be construed as limited to the particulars of the proposals specifically described above, but is to be afforded the full scope defined by the accompanying claims.

I claim:

1. In a mineral exploration survey wherein a sievable bulk sample of a sedimentary deposit containing a minute amount of an economic mineral is collected from a survey site, then processed and subsequently analyzed to detect the presence of said mineral, an improved method of processing said sample after said collection and prior to said analysis, said method comprising the steps of:
   (a) washing and wet sieving the sample with water containing an additive to reduce particle cohesion, and thereby obtaining at least two size fractions of said sample;
   (b) drying at least one of said size fractions; and
   (c) separating with heavy liquid said last mentioned size fraction into at least two specific gravity fractions.

2. A method as defined in claim 1, further including a magnetic separation step applied to at least one of said two specific gravity fractions.

3. A method as defined in claim 2, wherein said at least one of said size fractions is a fine size fraction consisting of clay size particles and other fine size particles, and wherein, prior to said specific gravity separation, said fine size fraction is resieved in a dry state thereby tending to strip any of said clay size particles adhered to fine size particles.

4. A method as defined in claim 1, further including magnetically separating at least one of said two specific gravity fractions into a magnetic fraction, a paramagnetic fraction, and a non-magnetic fraction.

5. A method as defined in claim 4, wherein at least a portion of said sample is heat treated for the purpose of increasingly magnetizing particles in said portion.

6. A method as defined in claim 4, wherein said at least one of said size fractions is a fine size fraction consisting of clay size particles and other fine size particles, and wherein, prior to said specific gravity separation, said fine size fraction is resieved in a dry state thereby tending to strip any of said clay size particles adhered to said fine size particles.

7. A method as defined in claim 1, wherein a plurality of said fractions produced by washing and wet sieving are dried and wherein each size fraction of said plurality of size fractions is separated into at least two specific gravity fractions.

8. A method as defined in claim 7, further including a magnetic separation step applied to at least one of said two specific gravity fractions of each size fraction of said plurality of size fractions.

9. A method as defined in claim 7, further including magnetically separating at least one of said two specific gravity fractions of each size fraction of said plurality of size fractions into a magnetic fraction, a paramagnetic fraction, and a non-magnetic fraction.

10. A method as defined in claim 7, wherein each of said plurality of size fractions is separated into a relatively light specific gravity fraction, a relatively heavy specific gravity fraction, and an intermediate specific gravity fraction intermediate said relatively light and said relatively heavy specific gravity fractions.

11. A method as defined in claim 10, further including a magnetic separation step applied to the heavy specific gravity fraction of each size fraction of said plurality of size fractions.

12. A method as defined in claim 11, further including a magnetic separation step applied to the intermediate specific gravity fraction of each size fraction of said plurality of size fractions.

13. A method as defined in claim 10, further including magnetically separating the heavy specific gravity fraction of each size fraction of said plurality of size fractions into a magnetic fraction, a paramagnetic fraction, and a non-magnetic fraction.

14. A method as defined in claim 13, further including magnetically separating the intermediate specific gravity fraction of each size fraction of said plurality of size fractions into a magnetic fraction, a paramagnetic fraction, and a non-magnetic fraction.

15. A method as defined in claim 14, wherein at least a portion of said sample is heat treated for the purpose of increasingly magnetizing particles in said portion.

16. A method as defined in claim 13, wherein at least a portion of said sample is heat treated for the purpose of increasingly magnetizing particles in said portion.

17. A method as defined in claim 1, wherein said at least one size fraction is separated into a relatively light specific gravity fraction, a relatively heavy specific gravity fraction, and an intermediate specific gravity fraction intermediate said relatively light and said relatively heavy specific gravity fractions.

18. A method as defined in claim 17, further including a magnetic separation step applied to said relatively heavy specific gravity fraction.

19. A method as defined in claim 18, further including a magnetic separation step applied to said intermediate specific gravity fraction.

20. A method as defined in claim 17, further including magnetically separating said heavy specific gravity fraction into a magnetic fraction, a paramagnetic fraction, and a non-magnetic fraction.

21. A method as defined in claim 20, wherein at least a portion of said sample is heat treated for the purpose of increasingly magnetizing particles in said portion.

22. A method as defined in claim 20, further including magnetically separating said intermediate specific gravity fraction into a magnetic fraction, a paramagnetic fraction, and a non-magnetic fraction.

23. A method as defined in claim 22, wherein at least a portion of said sample is heat treated for the purpose of increasingly magnetizing particles in said portion.

24. A method as defined in claim 1, wherein prior to said step of drying at least a portion of said sample is panned with a mechanical panner in water containing an additive which reduces the surface tension of the water.

25. In a mineral exploration survey wherein a sievable bulk sample of a sedimentary deposit containing a minute amount of an economic mineral is collected from a survey site characterized by unstable sulphide conditions, then processed and subsequently analyzed to detect the presence of said mineral, an improved method of processing a portion of said sample after said collection and prior to said analysis, said method comprising the steps of:
    (a) washing and wet sieving the portion with water containing an additive to reduce particle cohesion and thereby obtaining at least two size fractions of said portion;
    (b) drying at least one of said size fractions;
    (c) separating with heavy liquid said last mentioned size fraction into at least two specific gravity fractions; and
    (d) separating at least a portion of one of said specific gravity fractions into a gangue fraction and an ore metal concentrate fraction by means of an acid leach.

26. A method as defined in claim 25, further including a magnetic separation step applied to one of said specific gravity fractions to provide a paramagnetic fraction thereof, said acid leach separation then being applied to said paramagnetic fraction.

27. A method as defined in claim 26, wherein said acid leach separation comprises the steps of:
    (a) submitting said portion of said specific gravity fraction to cold aqua regia digestion;
    (b) adding oxalic acid to the digested portion and boiling the resulting acid mixture;
    (c) filtering the resulting hot acid solution;
    (d) evaporating the filtered solution to dryness to produce a solute; and
    (e) heating the solute to decompose free oxalic acid and to drive off water of hydration.

28. A method as defined in claim 25, wherein said acid leach separation comprises the steps of:
    (a) submitting said portion of said specific gravity fraction to cold aqua regia digestion;
    (b) adding oxalic acid to the digested portion and boiling the resulting acid mixture;
    (c) filtering the resulting hot acid solution;
    (d) evaporating the filtered solution to dryness to produce a solute; and
    (e) heating the solute to decompose free oxalic acid and to drive off water of hydration.

29. In a geochemical orientation survey wherein a sievable bulk sample of a sedimentary deposit containing a minute amount of an economic mineral is collected from a survey site, then processed and subsequently analyzed to detect the presence of said mineral, an improved method of processing said sample after said collection and prior to said analysis for the purpose of increasing the concentration of said mineral in at least one fraction of such sample, said method comprising the steps of;
    (a) washing and wet sieving the sample to reduce particle cohesion, to substantially remove any clay size cohesive particles, and to isolate at least one size fraction of said sample of size less than 6 mesh;
    (b) drying said last mentioned size fraction;
    (c) separating with heavy liquid said last mentioned size fraction into at least two specific gravity fractions; and
    (d) magnetically separating at least one of said specific gravity fractions in a magnetic field for the purpose of separating any significant quantities of paramagnetic particles from any quantities of non-magnetic particles.

30. A method as defined in claim 29, wherein the step of washing and wet sieving is done with water containing a detergent additive.

31. A method as defined in claim 29, wherein the step of magnetically separating includes at least two magnetic separations to produce a magnetic fraction of said at least one specific gravity fraction, a paramagnetic fraction of said at least one specific gravity fraction, and a non-magnetic fraction of said at least one specific gravity fraction.

32. A method as defined in claim 31, wherein at least a portion of said sample is heat treated for the purpose of increasingly magnetizing particles in said portion.

33. A method as defined in claim 29, wherein at least one of the fractions produced is analyzed for the purpose of detecting economic mineral concentration in such fraction.

34. A method as defined in claim 29, wherein prior to said step of drying at least a portion of said sample is panned with a mechanical panner in water containing an additive which reduces the surface tension of the water.

35. In a mineral reconnaissance survey wherein sievable sediments containing gangue particles and a minute amount of economic mineral particles are collected from a survey site, then processed and subsequently analyzed to detect the presence of said mineral, an improved method of processing said sediments after said collection and prior to said analysis for separating economic mineral particles from gangue particles, said method comprising the steps of:
    (a) washing and wet sieving a bulk sample of the sediments to reduce particle cohesion, to substantially remove any clay size cohesive particles and to isolate at least one size fraction of said sample of size less than 6 mesh;
    (b) drying said last mentioned size fraction;
    (c) separating with heavy liquid said last mentioned size fraction into a least two specific gravity fractions.

36. A method as defined in claim 35, wherein at least one of said specific gravity fractions is magnetically separated.

37. A method as defined in claim 35, wherein at least one of said specific gravity fractions is magnetically separated to produce a magnetic fraction thereof, a paramagnetic fraction thereof, and a non-magnetic fraction thereof.

38. A method as defined in claim 37, wherein at least a portion of said sample is heat treated for the purpose of increasingly magnetizing particles in said portion.

39. A method as defined in claim 35, wherein prior to said step of drying at least a portion of said sample is panned with a mechanical panner in water containing an additive which reduces the surface tension of the water.

40. A method as defined in claim 35, wherein at least one of the fractions produced is analyzed for the purpose of detecting economic mineral concentration in such fraction.

* * * * *